(12) United States Patent
Visvikis-Siest et al.

(10) Patent No.: US 10,697,017 B2
(45) Date of Patent: Jun. 30, 2020

(54) GENETIC FACTORS IN BLOOD PRESSURE

(71) Applicant: RANDOX LABORATORIES LTD., Crumlin (GB)

(72) Inventors: Sophie Visvikis-Siest, Nancy (FR); Said El Shamieh, Nancy (FR); Helena Murray, Crumlin (GB); John Lamont, Crumlin (GB); Peter Fitzgerald, Crumlin (GB)

(73) Assignee: RANDOX LABORATORIES LTD., Crumlin (GB)

( * ) Notice: Subject to any disclaimer, the term of this patent is extended or adjusted under 35 U.S.C. 154(b) by 498 days.

(21) Appl. No.: 14/367,510

(22) PCT Filed: Dec. 21, 2012

(86) PCT No.: PCT/EP2012/076832
§ 371 (c)(1),
(2) Date: Jun. 20, 2014

(87) PCT Pub. No.: WO2013/093091
PCT Pub. Date: Jun. 27, 2013

(65) Prior Publication Data
US 2014/0336283 A1    Nov. 13, 2014

(30) Foreign Application Priority Data
Dec. 23, 2011  (GB) .................................. 1122228.8

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2010/0035983 A1*  2/2010  Shiffman ............. C12Q 1/6883
                                                    514/510
2011/0033444 A1    2/2011  Chang et al.

OTHER PUBLICATIONS

Watfa (Dementia and Geriatic Cognitive Disorders, 2010, 30:440-448).*
El Shamieh, S. et al. "Functional Epistatic Interaction between rs6046G>A in F7 and rs5355C>T in SELE Modifies Systolic Blood Pressure Levels" PLoS ONE, 2012, 7(7):e40777.
Faruque, M. et al. "Association of ATP1B1, RGS5 and SELE polymorphisms with hypertension and blood pressure in African-Americans" J. Hypertens., 2011, 29(10):1906-1912.
Okuda, T. et al. "Verification of 525 coding SNPs in 179 hypertension candidate genes in the Japanese population: identification of 159 SNPs in 93 genes" J. Hum. Genet., 2002, 47:387-394.
Sass, C. et al. "Relationship between E-selectin L/F554 polymorphism and blood pressure in the Stanislas cohort" Hum. Genet., 2000, 107:58-61.
Sass, C. et al. "Association Between Factor VII Polymorphisms and Blood Pressure: The Stanislas Cohort" Hypertension, 2004, 44:674-680.

* cited by examiner

*Primary Examiner* — Sarae L Bausch
(74) *Attorney, Agent, or Firm* — Saliwanchik, Lloyd & Eisenschenk

(57) ABSTRACT

The invention describes epistatic interactions between single nucleotide polymorphisms on genes associated with blood pressure and provides an application for their use in a method to determine an individual's susceptibility to hypertension and hence whether anti-hypertensive treatment will be beneficial for said individual. In addition gene expression levels are also linked to blood pressure and may also be used to determine susceptibility to hypertension.

3 Claims, 1 Drawing Sheet

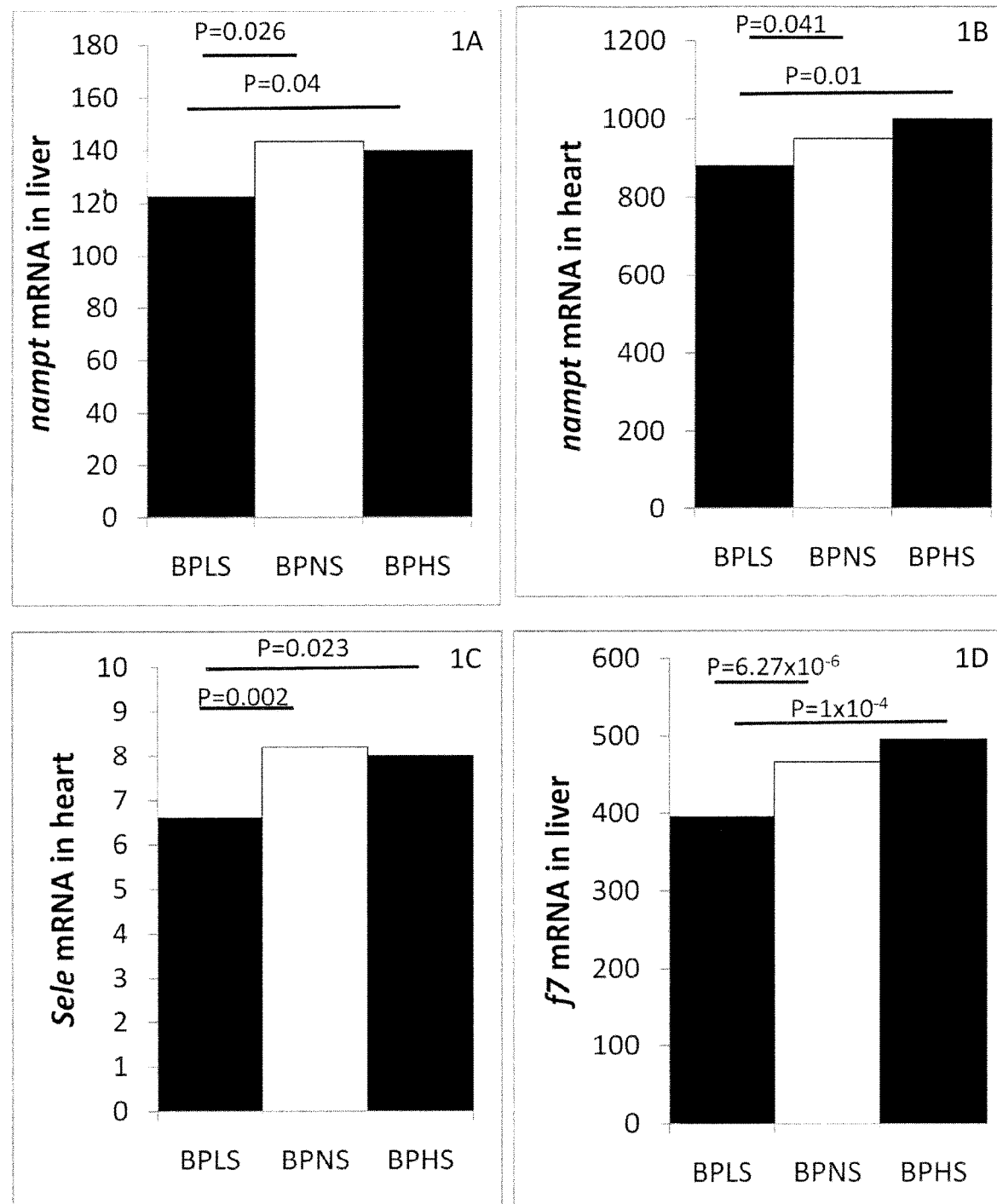

GENETIC FACTORS IN BLOOD PRESSURE

CROSS-REFERENCE TO RELATED APPLICATION

The present application is the National Stage of International Application No. PCT/EP2012/076832, filed Dec. 21, 2012, which is hereby incorporated by reference herein in its entirety, including any FIGURES, tables, nucleic acid sequences, amino acid sequences, and drawings.

BACKGROUND TO THE INVENTION

Hypertension (HTN) is a worldwide disease [1]. Population-based studies showed that 972 million adults were hypertensive in 2005 and it is predicted to increase, by about 60% to 1.56 billion by 2025 [2]. Even at early stages, it is a major cause of disability and death for millions of people [3]. Observational studies involving more than 1 million adults from 61 prospective studies have indicated that death from HTN associated cardiovascular diseases (CVDs), both ischemic heart disease and stroke, increases linearly from blood pressure (BP) levels as low as 115/75 mmHg among middle-aged and elderly individuals [4].

BP is a heritable trait with estimates indicating that 30-70% of its variance is attributable to genetic variations [5]. In family studies it varies from ≈31% (single-measure of systolic blood pressure (SBP) and diastolic blood pressure (DBP)), to ≈57% (long-term average of SBP and DBP phenotype) and to ≈68% (24-hour profile of SBP and DBP) [6]. Both BP and HTN are still considered polygenic traits [5]. Inflammation, blood coagulation cascade, cellular adhesion molecules and lipid metabolism all appear to have significant roles [7].

The largest Genome-wide association study (GWAS) on blood pressure including ≈270,000 individuals was recently published [8], reporting 28 loci to be associated with SBP, DBP and/or HTN [8]. Their genetic risk score explained only 0.9% of BP phenotypic variance [8], this representing the so-called 'dark matter' of genetic risk [9]. A large 'hidden heritability' of unknown nature may be explained by rare variants, structural large variants, epistatic (G*G) and gene*environment interactions [9]. Epistatic interactions may also play an important role in discovering genes that have not yet been found by the consensual single-locus approach [9]. This statement has been extensively reviewed in the last years and both parametric and nonparametric multi-locus methods have been developed to detect such interactions [9]. Epistatic interactions have been documented for susceptibility to cancer [10], morphology [11] and autoimmune conditions [12]. However, to date they have not been extensively studied in HTN and the underlying genetic basis for hypertension remains poorly understood.

REFERENCES

1. Takeuchi F, et al. (2010) Circulation 121:2302-9.
2. Kearney P. M, et al. (2005) Lancet; 365:217-23.
3. El Shamieh S, et al. (2010) Clin Chim Acta. 413, 1-2:34-38.
4. Chobanian A. V, et al. (2003) Hypertension; 42:1206-52.
5. Levy D, et al. (2000) Hypertension; 36:477-83.
6. Ehret G. B. (2010) Curr Hypertens Rep; 12:17-25.
7. Visvikis-Siest S, et al. (2007) Clin Chem Lab Med; 45:1154-68.
8. Ehret G. B, et al. (2011) Nature; 478:103-9.
9. Ndiaye N. C, et al. (2011) Clin Chim Acta; 412:1697-701.
10. Fijneman R. J, et al. (1996) Nat Genet; 14:465-7.
11. Leamy L. J, et al. (2002) Evolution; 56:642-53.
12. Wandstrat A, Wakeland E. (2001) Nat Immunol; 2:802-9.
13. Benetos A, et al. (2002) Circulation; 105:1202-7.
14. Dasberg H, et al. (1962) Br Heart J; 24:214-20.
15. Chobanian A. V et al. (2003) Hypertension; 42:1206-52.
16. Visvikis-Siest S & Siest G. (2008) Clin Chem Lab Med; 46:733-47.
17. Miller S. A, et al. (1988) Nucleic Acids Res; 16:1215.
18. Zee R. Y, et al. (2006) Circulation; 113:2193-200.
19. Ramensky V, et al. (2002) Nucleic Acids Res; 30:3894-900.
20. Marteau J. B, et al. (2005) Clin Chem; 51:1250-2.
21. Van der Weele T. J. (2010) Stat Appl Genet Mol Biol; 9:Article.
22. Puig O, et al. (2010) Physiol Genomics; 42A:24-32.

SUMMARY OF THE INVENTION

The current invention illustrates epistatic interactions between single nucleotide polymorphisms on genes associated with blood pressure and provides an application for their use in a method to determine an individual's susceptibility to hypertension and hence whether anti-hypertensive treatment will be beneficial for said individual. In addition gene expression levels are also linked to blood pressure and may also be used to determine susceptibility to hypertension.

DESCRIPTION OF FIGURES

FIG. 1—NAMPT, SELE and F7 gene expression among blood pressure inbred mouse strains. A—Expression analysis of NAMPT mRNA showed increased expression in liver of BPNS (N=5) and BPHS (N=5) compared to BPLS (N=4). B—Expression analysis of NAMPT mRNA showed increased expression in heart of BPNS (N=5) and BPHS (N=5) compared to BPLS (N=4). C—Expression analysis of SELE mRNA showed increased expression in heart of BPNS (N=5) and BPHS (N=5) compared to BPLS (N=4). D—Expression analysis of F7 mRNA showed increased expression in liver of BPLS (N=4) and BPNS (N=5) compared to BPHS (N=5). (BPHS=blood pressure high strain, BPLS=blood pressure low strain, BPNS=blood pressure normal strain).

DETAILED DESCRIPTION

Unless otherwise stated technical terms are used according to the conventional usage as known to those skilled in the art.

The current invention provides a method of determining an individual's susceptibility to hypertension comprising analysing the SELE and/or F7 gene(s) in a sample taken from the individual, wherein the presence or absence of one or more single nucleotide polymorphisms on said gene(s) is related to the individual's susceptibility to hypertension.

The terms 'hypertension' or 'high blood pressure' as used herein refer to a chronic cardiac medical condition in which the systemic arterial blood pressure is elevated. It is classified as blood pressure which is above 140/90 mmHg. Hypertension can be categorised as primary (essential) hypertension, in which there is no obvious medical cause, or secondary hypertension, caused by underlying medical conditions affecting the heart, arteries, kidneys and/or endocrine system for example. As many as 95% cases of hypertension are categorised as primary hypertension.

The term 'blood pressure' as used herein refers to the pressure exerted by circulating blood upon the walls of blood vessels; most commonly it refers to the arterial pressure of systemic circulation and is measured at an individual's upper arm. A blood pressure reading gives two measurements, the first FIGURE is the systolic blood pressure which is the pressure in an individuals' arteries when the heart is contracting, the second lower FIGURE is the diastolic blood pressure which is the pressure in an individuals' arteries between heart beats. A normal blood pressure is considered to be approximately 120/80 mmHg. High blood pressure is an important risk factor in a number of conditions including stroke and myocardial infarction. 'SELE' as used herein refers to E-selectin, a cell adhesion molecule which is involved in inflammation. It is located at 1q22-q25 of chromosome 1 and has Gene ID 6401 (NCBI). 'F7' as used herein refers to Factor VII, a serine protease enzyme involved in the coagulation cascade. It is located at 13q34 of chromosome 13 and has Gene ID 2155 (NCBI).

Preferably the single nucleotide polymorphism(s) determined is/are rs5355C>T in the SELE gene and/or rs6046G>A in the F7 gene. Rs5355 is a missense single nucleotide polymorphism in which T is substituted for the wild-type C allele resulting in a codon which codes for phenylalanine instead of leucine. Rs6046 is a missense single nucleotide polymorphism in which A is substituted for the wild-type G allele resulting in a codon which codes for glutamine instead of arginine.

In a preferred embodiment of the current invention on analysing the SELE and/or F7 genes; i) the presence of a rs5355T allele in an individual is associated with decreased blood pressure compared to a reference group ii) the presence of a rs6046A allele in an individual is associated with decreased blood pressure compared to a reference group iii) the presence of one or more rs5355T alleles (rs5355CT, rs5355TC or rs5355TT) in combination with one or more rs6046A alleles (rs6046AG, rs6046GA or rs6046AA) is associated with increased blood pressure compared to a reference group. The preferred reference group is made up of individuals who are homozygous for the Wild-Type alleles for the SELE and/or F7 genes.

The presence/absence of the single nucleotide polymorphism may be determined at the nucleic acid or protein level using any method known to those skilled in the art. Examples of assays used to detect the SNP at the nucleic acid level include but are not limited to DNA microarrays, PCR assays and Fluorescent In-situ hybridization. Examples of assays used to detect the SNP at the protein level include but are not limited to ELISA, Western blots, Immunohistochemistry and High performance liquid chromatography.

The sample used to determine the presence/absence of an SNP of the current invention can be any biological sample from which the SNP can be determined as known to those skilled in the art, but is preferably selected from the group consisting of whole blood, serum, plasma, urine, saliva, tissue sample and hair.

An embodiment of the current invention is a method of investigating an individual's susceptibility to hypertension comprising determining the individual's expression level of NAMPT in a sample taken from the individual. The sample can be any biological sample from which NAMPT expression levels can be determined but is preferably whole blood, serum or plasma, most preferably the sample is peripheral blood mononuclear cells. 'NAMPT' as used herein refers to nicotinamide phosphoribosyltransferase which is a cytokine that promotes B cell maturation and inhibits neutrophil apoptosis, it is also known as visfatin and Pre B-cell colony enhancing factor I (PBEF1). In the preferred embodiment expression levels are compared to a reference amount and increased levels of NAMPT compared to said reference amount indicate that the individual is susceptible to hypertension. The reference amount can be NAMPT expression levels from individuals known to have normal or low blood pressure for example. In addition to NAMPT, expression levels of SELE and/or F7 in said individual can also be determined and any variations when compared to reference amounts can be informative towards hypertension susceptibility.

Another embodiment of the invention is a method of treating an individual with essential hypertension comprising administering pharmaceutically effective amounts of a compound which inhibits at least one SNP in the SELE and/or F7 genes at the nucleic acid level, or which inhibits a protein encoded by said SNP(s) or a combination of both.

A further embodiment of the invention is the use of a medicament to treat a hypertensive individual possessing either of the wt SELE or F7 genes or both the rs5355C>T SELE allele and one or more of the rs6046G>A F7 allele. The medicament could be for example a drug selected from the group of calcium channel blockers, renin-angiotensin system inhibitors, diuretics, adrenergic receptor antagonists, aldosterone antagonists, vasodilators, Alpha-2 agonists and pharmaceutically acceptable salts thereof. The medicament used to treat the hypertensive individual may also be a compound which inhibits the wt SELE gene, the wt F7 gene and either the rs5355C>T SELE gene or the rs6046G>A F7 gene.

It is anticipated that in a further embodiment a use of the current invention could be in combination with additional biomarkers for hypertension in a method for determining an individual's susceptibility to hypertension wherein an individuals' allelic makeup and/or gene expression levels indicate whether the individual is susceptible to hypertension and hence would benefit from anti-hypertensive therapy. In such a method wherein the individual is found to be predisposed to high blood pressure anti-hypertensive therapy can be implemented. The anti-hypertensive therapy could be a drug selected from the group of calcium channel blockers, renin-angiotensin system inhibitors, diuretics, adrenergic receptor antagonists, aldosterone antagonists, vasodilators, Alpha-2 agonists and pharmaceutically acceptable salts thereof and could also involve lifestyle changes such as lowering sodium intake.

Material and Methods

Ethics Statement

The samples were part of a human sample storage platform: the Biological Resources Bank (BRC) "Interactions Gène-Environnement en Physiopathologie CardioVasculaire" (BRC IGE-PCV) in Nancy, East of France. All individuals gave written informed consent and the project protocol was approved by the local ethics committee (Comité Consultatif de Protection des Personnes, CPP—Lorraine, France).

Study Population

The study enrolled 3,600 unrelated adults (47.4% women) aged 47.33±10.52. A sample of 2971 individuals was recruited during free medical check-ups at the Center of Preventive Medicine of Vandoeuvre-lès-Nancy in the East of France. They were Caucasians, born in France for three generations and their clinical and biological data were collected at entrance before any eventual drug prescription following consultation. All subjects gave written informed consent. They were selected on the basis of the following criteria: (1) no antihypertensive drug therapy at recruitment; (2) complete clinical and genotypic data available; (3) and BP levels ranging from normotensive to stage 2 HTN (for hypertensive individuals, data were gathered before the prescription of any medication). Stage 3 HTN patients were excluded as they were all under anti-hypertensive medication.

As our purpose was to assess BP as a continuous trait, and in order to have a proper inter-individual variability, we included in our population study the ERA cohort (Evolution de la Rigidité Artérielle). Participants from this cohort were selected from a Parisian cohort that had a health checkup at the IPC (Investigations Préventives et Cliniques) center, which is one of the medical centers of the French national health care system (Securité Sociale-CNAM). The details of this study have been presented previously [13]. The study population was composed of 629 participants aged between 25 and 88 years (mean age 52.21±10.44). All individuals signed an informed consent and the study protocol was approved by an ethics committee (Comité d'Ethique du Centre Hospitalier Universitaire de Cochin).

Clinical and Biological Data Collection

SBP and DBP were measured under constant temperature (19° C.-21° C.) and standardized conditions (supine position) using a manual sphygmomanometer (Colonne à mercure, Mercurius) by expert nurses [13]. The recorded values were the means of 3 readings on 20 min intervals. An adjustable BP cuff was used to correct errors due to variations in arm circumference [14]. HTN was defined as SBP≥140 mmHg or DBP≥90 mmHg as recommended in the seventh Report of the Joint National Committee on the prevention, detection, evaluation, and treatment of high blood pressure [15]. All individuals underwent complete medical examination including anthropometric and biochemical measurements collected with standardized methods as described elsewhere [16].

Genotyping Assays

We selected rs1799752 Ins>del in ACE, rs5882 in CETP A>G, rs1801133C>T in MTHFR rs662A>G in PON1 and rs1800629G>A in TNF from the "Cardio-Vascular Disease 35" assay, a multi-locus genotyping assay developed in collaboration with Roche Molecular Systems [13]. In addition, we chose rs5355 C>T in SELE, rs6046>A in F7, rs1800790G>A in FGB, rs328C>G in LPL based on our previous published results and rs3025058T>Ins in MMP3 from internal investigations in order to establish a new specific multilocus assay for HTN.

Genomic DNA was extracted from peripheral blood samples using the salting out method [17]. Genotyping was performed using two methods. 1) A multilocus assay with an immobilized probe approach (Roche Molecular Systems, Pleasanton, Calif., USA) [18]. After PCR amplification using pooled biotinylated primers and hybridization to sequence-specific oligonucleotide probes, genotype assignments were performed by two independent observers using proprietary Roche Molecular Systems image processing software. Among 2971 individuals, discordant results (<3% of all scoring) were resolved by a third observer and if necessary, by a joint reading. 2) Evidence Investigator™ biochip designed by Randox Laboratories, Antrim, UK was used to genotype ERA participants. This genotyping assay is based on a combination of probe hybridization, PCR amplification and microarray hybridization. This unique design permits high assay multiplexing and ready discrimination between genotypes.

Validation of Evidence Investigator™ genotyping results: Blinded replication analysis was performed on 50 common samples. Both genotyping methods gave matched results at 99%.

PolyPhen Analysis of Nonsynonymous SNPs

The prediction of nonsynonymous SNPs possible impacts on their protein structures was performed using PolyPhen (http://genetics.bwh.harvard.edu/pph2/) [19].

Peripheral Blood Mononuclear Cells Collection

Freshly drawn peripheral venous blood (10 ml) was collected into tubes containing EDTA (Vacutainer, Becton Dickinson) under fasting conditions. PBMCs were then isolated by centrifuging on a density gradient of Ficoll as described previously and stored at −80° C. until RNA extraction [20]. PBMCs bank with high recovery of lymphocytes (97.5%) was constituted as described elsewhere [20].

RNA Extraction and qRT-PCR Analysis

In a subsample of 175 individuals, total RNA was isolated from PBMCs by an automated isolation procedure (MagNa Pure LC instrument). mRNA quality and stability were carefully tested [20] and reverse transcribed as previously described [20]. Quantitative real-time PCR (qRT-PCR) was performed using LightCycler instrument (Roche Diagnostics, Mannheim, Germany) with Master Plus SYBR Green I kit for all gene transcripts. SELE and F7 were not quantified as they were not expressed in PBMCs. Specific primers were designed using Primer Premier 3.0 software (http://frodo.wi.mit.edu/primer3/). All experiments were carried out in duplicate in a total reaction volume of 20 μl containing 0.5 mM of each specific primer. Negative and internal controls were included. All mRNA levels were normalized to the mRNA levels of POL2RA. The specificity of all PCR products was further verified by electrophoresis on 10% polyacrylamide gel.

Statistical Analyses

Statistical analyses were performed using the SPSS® statistical software version 19.0 (SPSS, Inc, Chicago, Ill.). Polymorphisms with minor allele frequencies (MAF) less than 2% or deviating from Hardy-Weinberg equilibrium (HWE) were excluded from individual analyses. In order to determine the effect of the 10 selected genetic variants on SBP and DBP assuming additive models using the common wild type as the reference group; age, sex and body mass index (BMI)-adjusted linear regressions were performed for individual association analyses. The significance level was set at $P \leq 5 \times 10^{-3}$ due to multiple testing's.

Two-locus additive epistasis was defined as significant statistical interaction between two SNPs [21] and was determined when significant interaction existed on a linear additive model (P<0.05) adjusted for age, gender and BMI.

Gene Expression Analysis in Blood Pressure Inbred Mouse Strains

Paired baseline and final raw gene expression data from 3 BP different mouse strains [22] were obtained from publically available data on gene expression omnibus (GEO) dataset GDS3675 (http://www.ncbi.nlm.nih.gov/gds). The study consists of 38,384 expression profiles extracted from heart, and liver tissues of 14 male mice (12 week old). The study group was composed of 5 genetically hypertensive mouse "blood pressure high strain (BPHS)", 4 hypotensive mouse "blood pressure low strain (BPLS)", and 5 normotensives "blood pressure normal strain (BPNS)". Quantile normalization was applied to all microarrays and paired samples t-tests were performed.

Results

It was found that the SNPs, rs5355C>T in SELE and rs6046G>A in F7 showed associations with SBP and/or DBP respectively (P≤5×10$^{-3}$, Table 2). rs5355T allele in SELE was associated with 2.14 mmHg decrease in DBP (P=5.1×10$^{-3}$, Table 2), whereas rs6046A allele in F7 was associated with 3.71 mmHg and 3.73 mmHg decrease in SBP and DBP respectively (P=3.7×10$^{-3}$ and P=8.2×10$^{-4}$ respectively, Table 2).

TABLE 2

Genetic variants associated with blood pressure.

| Chromosome | Gene | SNP ID | MAF | P | Beta | BP mmHg | trait |
|---|---|---|---|---|---|---|---|
| 1q22-q25 | SELE | rs5355C > T | 0.04 | 0.005 | −0.3 | −2.14 | DBP |
| 13q34 | FVII | rs6046G > A | 0.1 | 0.004 | −0.55 | −3.7 | SBP |
|  |  |  |  | 0.001 | −0.78 | −3.73 | DBP |

SNP: single nucleotide polymorphism, MAF: minor allele frequency, Beta: coefficient in the linear regression model, SBP: systolic blood pressure, DBP: diastolic blood pressure.

Whereas rs5355C>T in SELE was not associated with any of the 13 transcripts, rs6046A allele in F7 was positively associated with NAMPT mRNA levels (P=9.2×10$^{-5}$, β=0.489). Table 3 shows G*G interaction between rs5355C>T in SELE and rs6046G>A in F7 in order to influence SBP and DBP (P=0.048 and P=0.047 respectively, Table 3). This interaction was also associated with NAMPT mRNA levels (P=1.1×10$^{-5}$ and P=0.02 for rs6046G>A in F7 and rs5355C>T in SELE respectively). It was found that individuals carrying rs5355T allele in SELE and rs6046GG in F7 had 6.53 mmHg and 8.04 mmHg decrease in DBP and SBP respectively. In contrast, individuals carrying rs5355T allele in SELE and one minor allele of rs6046G>A (rs6046GA) had 1.07 mmHg and 1.16 mmHg increase in DBP and SBP respectively. Furthermore, carriers of rs5355T allele in SELE and two minor alleles of rs6046G>A (rs6046AA) had higher BP levels when compared with those carrying one minor allele, which had 5.1 mmHg and 3.77 mmHg increase in DBP and SBP respectively. We concluded that rs6046A may invert the beneficial effect of rs5355T on DBP and SBP via NAMPT mRNA levels.

TABLE 3

Blood pressure variations according to rs5355C > T in SELE and rs6046G > A in F7 interaction.

| | | SELE | | | | |
|---|---|---|---|---|---|---|
| | DBP | rs5355T | P | SBP | rs5355T | P |
| F7 | rs6046GG | −6.53 mmHg | 0.047 | rs6046GG | −8.04 mmHg | 0.048 |
| | rs6046GA | 1.07 mmHg | | rs6046GA | 1.16 mmHg | |
| | rs6046AA | 5.1 mmHg | | rs6046AA | 3.77 mmHg | |

SBP: systolic blood pressure, DBP: diastolic blood pressure.

Analysis of gene expression profiles from liver and heart of 3 different BP inbred mouse strains, revealed significantly different mRNA levels regarding BP levels (FIG. 1). NAMPT mRNA was higher in liver and heart of BPLS compared to BPNS (P=0.026 and P=0.041 respectively, FIG. 1A) and BPHS (P=0.04 and P=0.01 respectively, FIG. 1B). SELE mRNA showed decreased expression in heart of BPLS compared to BPNS (P=0.002, FIG. 1C) and BPHS (P=0.023, FIG. 1C). F7 mRNA showed decreased expression in liver of BPHS compared with BPLS (P=6.27×10$^{-6}$, FIG. 1D) and BPNS (P=1×10$^{-4}$, FIG. 1D).

We claim:

1. A method of treating an individual predisposed to high blood pressure comprising:
   (a) obtaining a biological sample from the individual, wherein the individual has not been treated with anti-hypertensive drug therapy;
   (b) determining whether a rs5355C>T single nucleotide polymorphism in the SELE gene is present or absent in the biological sample by contacting the biological sample with a nucleic acid probe that hybridizes to the rs5355C>T single nucleotide polymorphism, wherein the rs5355C>T single nucleotide polymorphism is determined to be present;
   (c) determining whether a rs6046G>A single nucleotide polymorphism in the F7 gene is present or absent in the biological sample by contacting the biological sample with a nucleic acid probe that hybridizes to the rs6046G>A single nucleotide polymorphism, wherein the rs6046G>A single nucleotide polymorphism is determined to be present;
   (d) after said determining of (b) and (c), determining the individual is predisposed to high blood pressure; and
   (e) administering to the individual determined to have both the rs5355C>T and rs6046G>A single nucleotide polymorphism an anti-hypertensive therapy selected from the group consisting of a calcium channel blocker, renin-angiotensin system inhibitor, diuretic, adrenergic receptor antagonist, aldosterone antagonist, vasodilator, and alpha-2 agonist.

2. The method of claim 1, wherein the biological sample of (a) is selected from the group consisting of whole blood, serum, plasma, urine, saliva, tissue sample, and hair.

3. The method of claim 1, wherein said determining of (b) and (c) is conducted with an assay selected from among DNA microarray, polymerase chain reaction, and fluorescent in-situ hybridization.

* * * * *